United States Patent
Shimizu

(10) Patent No.: US 6,589,257 B1
(45) Date of Patent: *Jul. 8, 2003

(54) ARTIFICIAL NEURAL TUBE

(75) Inventor: Yasuhiko Shimizu, Uji (JP)

(73) Assignee: Tapic International Co., Ltd., Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 09/719,271

(22) PCT Filed: Jun. 7, 1999

(86) PCT No.: PCT/JP99/03018

§ 371 (c)(1),
(2), (4) Date: Dec. 8, 2000

(87) PCT Pub. No.: WO99/63908

PCT Pub. Date: Dec. 16, 1999

(30) Foreign Application Priority Data

Jun. 10, 1998 (JP) .......................... 10-162397

(51) Int. Cl.[7] ............................................. A61B 17/08
(52) U.S. Cl. ........................................ 606/152; 623/12
(58) Field of Search ............................. 606/152; 623/12

(56) References Cited

U.S. PATENT DOCUMENTS

| | | | |
|---|---|---|---|
| 5,656,605 A | * | 8/1997 | Hansson et al. ............ 424/423 |
| 6,090,117 A | * | 7/2000 | Shimizu ..................... 606/152 |
| 6,335,007 B1 | * | 1/2002 | Shimizu et al. ............. 424/422 |

FOREIGN PATENT DOCUMENTS

| | | | |
|---|---|---|---|
| JP | 60-34450 | 2/1985 | |
| JP | 2-109569 A | 4/1990 | |
| JP | 2-502432 A | 8/1990 | |
| JP | 06-292716 A | 10/1994 | ........... A61L/27/00 |
| JP | 6-292716 A | 10/1994 | |
| JP | 7-501465 A | 2/1995 | |
| WO | PCT/WO88/06871 | 9/1988 | ............. A61F/2/04 |

OTHER PUBLICATIONS

Tong, et al., "Sciatic Nerve Regeneration Navigated by Laminin–Fibronectin Double Coated Biodegradable Collagen Grafts in Rats," Brain Research, vol. 663, No. 1 (1994), pp. 155–162.

Tong, et al., "Sciatic Nerve Regeneration Navigated by Lamin–Fibronectin Double Coated Biodegradable Collagen Grafts in Rats", Brain Research, vol. 663, No. 1 (1994) pp. 155–162.

* cited by examiner

Primary Examiner—Andrew M. Falik
Assistant Examiner—Robert H. Muromoto, Jr.
(74) Attorney, Agent, or Firm—Edwards & Angell, LLP; Peter F. Corless, Esq.; Richard J. Roos, Esq.

(57) ABSTRACT

An artificial tube for a nerve is disclosed that has a controlled rate of decomposition in the body such that the tube remains in the body until the nerve regenerates, which induces axons regenerated from severed nerve stumps to extend in the proper direction without pressing on the regenerated nerve following nerve regeneration and causes rapid restoration of blood flow by promoting infiltration of blood capillaries from the body to promote regeneration of the nerve, and which comprises a tube (10) or (20) having a coating layer (13) or (23) that is composed of gelatin or collagen on at least the outer surface of tube (11) or (21) that is composed of a material that is biodegradable and absorbable in vivo, wherein a pre-thermal dehydration crosslinking treated collagen fiber bundle (referring to a bundle fibers (31) composed of collagen) is inserted in its lumen along the axis of the tube (10) or (20), and wherein the fibers composed of collagen are coated with laminin.

5 Claims, 1 Drawing Sheet

ARTIFICIAL NEURAL TUBE

TECHNICAL FIELD

The present invention relates to an artificial tube for nerve.

BACKGROUND ART

In the case of peripheral nerve being severed surgically or severed due to injury, an initial attempt is made to directly anastomose the stumps of the severed peripheral nerve. In many cases, however, it is impossible to accurately anastomose the severed nerve directly resulting in the nerve being left in the severed state. Consequently, although the nerve attempts to regenerate towards the distal side, it is impaired by connective tissue. Hence, regeneration stops with the formation of a neuroma at the severed end without reaching the neural stump on the distal side. As a result, the function of the severed nerve is frequently not restored after the surgical wound or injury has healed, and sequella remain. In cases in which direct anastomosis is impossible, a peripheral nerve having a function which is not very important may be partially excised from the same patient, and autotransplantation may be performed to the severed site of the nerve using this peripheral nerve segment. However, in this method as well, not only are there many cases in which nerve function is not adequately restored, but there are also many cases in which decreased function is observed even at the portion at which the transplanted nerve is used.

Therefore, numerous attempts have been made to restore function by connecting the stumps of severed peripheral nerves with a tube-shaped medical material, namely an artificial tube for nerve, regenerating the axon from the stump on the central side of the nerve trunk towards the stump on the distal side, inducing the nerve to extend in the proper direction, and allowing the nerve to reach a myoneural junction or peripheral sensory receptor from the peripheral nerve trunk. In the past, various materials have been attempted to be used as artificial tube for nerve, examples of which include non-porous tubes made of silicone, polyethylene or polyvinyl chloride, porous tubes made of drawn polytetrafluoroethylene or cellulose, semipermeable membrane tubes made of polyacrylonitrile or polysulfone, tubes made of biodegradable materials such as polyglycolic acid, polylactic acid or their copolymers, gelatin tubes, or biological tissue tubes originating in the same species such as arteries and veins. However, in regeneration experiments on peripheral nerves using these materials, since biological repair is impaired by the material, the length of nerve that has been able to be regenerated thus far has been at most on the order of 15 mm. In addition, not only is the regenerated nerve narrow without the form of the nerve being normally restored, but there are also many cases in which the function of regenerated nerve is not restored. In addition, although examples have been reported in which neural growth factor NGF is filled into a tube, since NGF ends up rapidly running out of the tube and dispersing, remarkable effects have not been obtained.

Although artificial tubes for nerve which comprise collagen tubes in which collagen fibers on which laminin and fibronectin are coated are filled (Tong, X., et al., Brain Research 663: 155–162 (1994), have recently been attempted, since the collagen tubes are unable to remain without being broken down until the nerve is regenerated to an adequate length, satisfactory results have not been obtained.

On the other hand, the spinal cord is considered to not regenerate once it has been damaged. In the case the spinal cord is damaged due to injury or tumor, the damaged spinal cord does not regenerate, and all function below the damaged portion is lost with paralysis remaining as the sequella. Recently however, experiments on animals have begun to be conducted that prove that the spinal cord is also able to regenerate. In the case where the spinal cord is severed sharply and accurately re-sutured, function is restored and the damaged portion is repaired to a considerable degree. In addition, if a portion of the spinal cord is excised in the form of a tube and an intercostal nerve fasicle is implanted at that site, the portion of the spinal cord regenerates and function is at least partially restored. If a portion of the spinal cord is excised in the form of a tube, and fetal spinal cord is transplanted to that site, spinal cord function and form are restored. These findings have been observed in experiments in rats. In this case as well, it is recognized that regeneration occurs only in the case where the transplanted fetal spinal cord segment is transplanted by properly aligning the respective neural processes. Based on the above findings, although it has been determined that regeneration of the spinal cord can occur by inducing the spinal cord so as to properly align the compartments of regenerated tissue, there have been no artificial tubes for spinal cord developed whatsoever that actually allow spinal cord regeneration.

Therefore, in order to control the rate of decomposition in the body so as to remain in the body until the nerve regenerates while also allowing degradation and absorption in the body as nerve regeneration progresses, the development of an artificial tube for nerve is desired that induces axons regenerated from severed nerve stumps to extend in the proper direction without pressing on the regenerated nerve following nerve regeneration, and causes rapid restoration of blood flow by promoting infiltration of blood capillaries from the body to promote regeneration of nerve tissue. In addition, there is also an urgent need for the development of an artificial tube for spinal cord that connects not only peripheral nerves but also the missing portions of spinal cord, and promotes proper regeneration of spinal cord tissue along with restoration of function.

DISCLOSURE OF THE INVENTION

The present invention relates to an artificial tube for nerve which comprises tube 10 or 20 having a coating layer 13 or 23 composed of gelatin or collagen on at least the outer surface of tube 11 or 21 composed of a material that is biodegradable and absorbable in vivo, and a pre-thermal dehydration crosslinking treated collagen fiber bundle (referring to a bundle of fibers 31 composed of collagen) inserted in its lumen along the axis of said tube; wherein said fibers composed of collagen being coated with laminin. The present invention also relates to a method for producing the above-mentioned artificial tube for nerve comprising: preparing a bundle of pre-thermal dehydration crosslinking treated collagen fibers 31, coating the surface of each fiber 31 that composes said collagen fiber bundle with laminin, producing tube 10 or 20 having a coating layer 13 or 23 composed of gelatin or collagen on at least the outer surface of tube 11 or 21 composed of a material that is biodegradable and absorbable in vivo, inserting a collagen fiber bundle composed of said laminin-coated collagen in said tube so as to be substantially parallel to the axis of said tube, and performing thermal dehydration crosslinking treatment.

Figure 1:
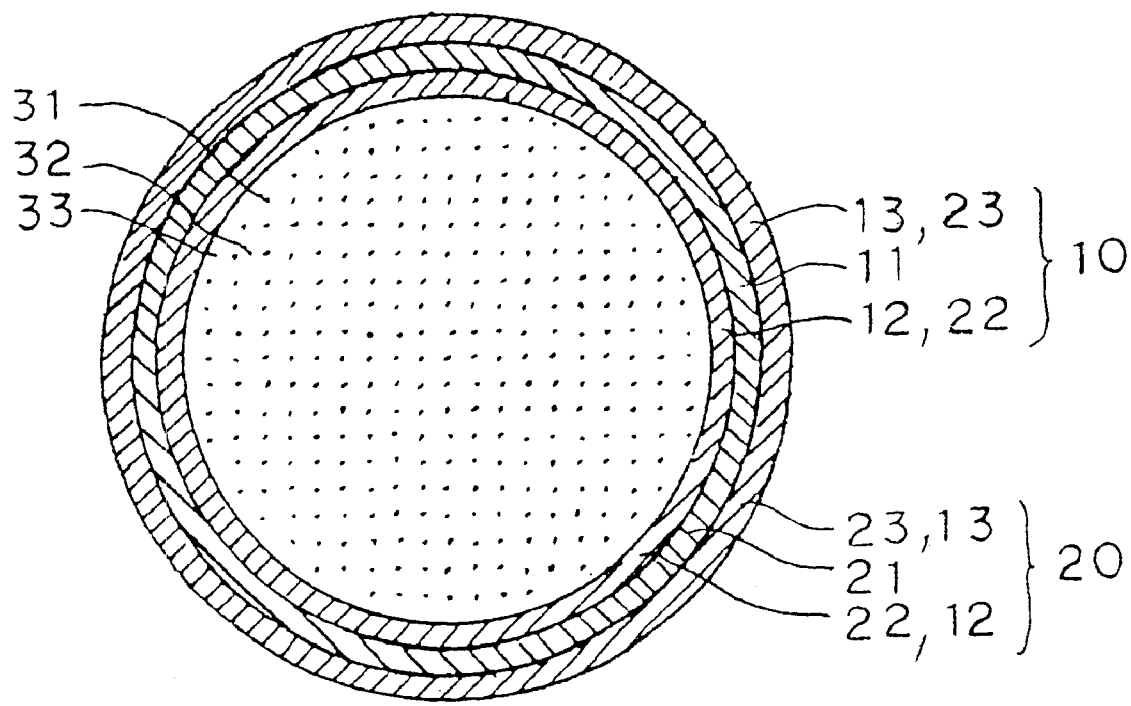
FIG. 1 is a drawing showing a cross-section of one of embodiments of an artificial tube for nerve of the present invention (that provides a schematic representation of the constitution without using actual dimensions).

The following reference numerals are used in the drawing.

11, 21: (Biodegradable, absorbable) tube
12, 13: (Gelatin) coating layer
22, 23: (Collagen) coating layer
31: Collagen fiber

BEST MODE FOR CARRYING OUT THE INVENTION

Although the length and inner diameter of the tube that composes the artificial tube for nerve of the present invention differs according to the length of the severed portion of the nerve and the thickness of the nerve, in order to cover, for example, a missing portion on the order of about 25 cm of the sciatic nerve of a cat, the length is about 28–35 mm, and preferably about 30 mm, and the inner diameter is about 1–8 mm, and preferably about 4 mm. In addition, in the case of using the artificial tube for nerve of the present invention as an artificial tube for spinal cord as well, the length of the tube is determined according to the length of the severed portion, while the inner diameter is preferably about 2–12 mm and particularly preferably about 10 mm.

It is necessary that the tube composed of a material that is biodegradable and absorbable in vivo that composes the artificial tube for nerve of the present invention retains the shape of the tube to prevent invasion of body cells from outside the tube during the time until the severed nerve regenerates and the severed location is rejoined (about 1–3 months). Consequently, a tube comprising a mesh material made of a material selected from the group consisting of polyglycolic acid, polylactic acid (L or DL), copolymer of glycolic acid and lactic acid, copolymer of lactic acid and ε-caprolactone, polydioxanone and copolymer of glycolic acid and trimethylene carbonate, which is able to maintain its shape in the body for a certain period of time despite being biodegradable and absorbable in vivo, is preferable, and a tube comprising a mesh material made of polyglycolic acid is particularly preferable. In addition, a tube comprising a material made of fine fibrous collagen can also be preferably used in addition to the tube comprising the mesh material made of a material that is biodegradable and absorbable in vivo such as polyglycolic acid.

To begin with, a description is provided of the artificial tube for nerve of the present invention having a coating layer 13 or 23 composed of gelatin or collagen on at least the outer surface of tube 11 comprising a mesh material made of a material such as polyglycolic acid that is biodegradable and absorbable in vivo. Although tube 11 comprising a mesh material made of polyglycolic acid has an inner diameter and length as described above, in order to allow it to retain the tubular shape of the artificial tube for nerve for about 1–3 months, the thickness of said tube (referring to the thickness of the tube wall in the form of a cylinder, and to apply similarly hereinafter) is preferably about 0.1–3 mm, and particularly preferably about 0.5–2 mm. If the thickness exceeds 3 mm, the tube obstructs regeneration of body tissue, and if the thickness is less than 0.1 mm, degradation and absorption of the tube proceed too rapidly, and the shape of the tube is not maintained until the nerve finishes regenerating. In addition, in the case of using the artificial tube for nerve of the present invention as an artificial tube for spinal cord, its thickness should preferably be about 0.2–5 mm, and particularly preferably about 0.5–3 mm.

In the case where the material that is biodegradable and absorbable in vivo is a material such as polyglycolic acid, the tube 11 is in the form of a mesh to ensure water permeability for hydrophobic tube 11. The mesh pore size of this mesh tube 11 is preferably about 5–30 μm, and particularly preferably about 10–20 μm. If the mesh pore size is less than about 5 μm, cells and tissue are unable to proliferate, while if the mesh pore size exceeds about 30 μm, entry of tissue becomes excessive.

In the case of the tube 11 comprising a mesh material made of a material such as polyglycolic acid, although it has a coating layer 13 or 23 composed of gelatin or collagen, which are materials having tissue regeneration promoting action, on at least the outer surface of tube 11 since it itself has no action that promotes tissue regeneration, it is particularly preferable that the inside of said tube and the inside surfaces of the mesh pores also be coated in addition to the outer surface of tube 11. The thickness of the coating layer 13 or 23 (and 12 or 22 in the case of inner surfaces as well) is preferably about 0.2–5 mm, and particularly preferably 0.5–3 mm, in the case of the collagen coating layer, and preferably about 0.2–5 mm, and particularly preferably 0.5–3 mm, in the case of the gelatin coating layer. Examples of such materials that promote tissue regeneration include collagen or gelatin which have water-permeability, do not cause foreign body reactions when applied in the body, have excellent bioaffinity and tissue compatibility, and have an action that promotes tissue regeneration. Collagen originating in various animals conventionally used in the past can be used for the collagen raw material, preferable examples of which include type I collagen or a mixture of type I and type III collagen originating in the skin, bone, cartilage, tendon and organs of cows, pigs, rabbits, sheep, kangaroos or birds that is solubilized by acid, base, enzymes and so forth. The coating layers composed of collagen are layers having an amorphous structure in which collagen molecules are dispersed. Purified gelatin according to the Japanese Pharmacopoeia can be used for the raw material of the coating layers composed of gelatin.

In the artificial tube for nerve of the present invention, the tube 11 or 21 composed of a material being biodegradable and absorbable in vivo can be the tube 11 composed of a mesh material made of a material such as the above-mentioned polyglycolic acid, or the tube 21 composed of a material made of fine fibrous collagen that uses collagen having tissue regeneration promoting action for its raw material. The following provides a description of the artificial tube for nerve of the present invention in which the material that is biodegradable and absorbable in vivo is a material composed of fine fibrous collagen, and a coating layer 23 (and also 22 depending on the case) of tube 21 is composed of collagen.

Type I collagen or a mixed collagen of type I and type III of animal origin like that described above that has been used in the past and is solubilized by acid, base or enzymes and so forth is preferable for the collagen used for the raw material of the material that is biodegradable and absorbable in vivo. This material composed of fine fibrous collagen is a matrix or thread-like woven or knitted product of a non-woven fabric-like multi-element structure in which fine fibers composed of collagen molecules are overlapped in multiple layers, and tube 21, which uses this as its material, has an inner diameter and length like those described above. The thickness is preferably about 0.5–5 mm, and particularly preferably about 1–2 mm, and in the case of using the artificial tube for nerve of the present invention as an artificial tube for spinal cord, its thickness is preferably about 0.5–5 mm, and particularly preferably about 1–3 mm. In addition, a coating layer 23 (and also 22 depending on the case) composed of collagen formed on at least the outer surface of this tube 21 uses conventional solubilized type I or a mixed collagen of type I and type III of animal origin as previously described, for its raw material, and has an amorphous structure in which collagen molecules are dispersed therein. The thickness of the coating layer is preferably about 0.1–2 mm, and particularly preferably about 0.5–1 mm.

The artificial tube for nerve of the present invention comprises a tube 10 or 20 having a coating layer 13 or 23 (and also 12 or 22 depending on the case) composed of gelatin or collagen on at least the outer surface of tube 11 or 21 composed of a material that is biodegradable and absorbable in vivo as was previously described in detail, and a bundle of collagen fibers 31 within its lumen that is inserted nearly in parallel with the axis of tube 10 or 20 and subjected in advance to thermal dehydration crosslinking treatment. Moreover, each of said collagen fibers is coated with laminin. When this artificial tube for nerve is applied in the body, the inner surface of the tube and surface of each collagen fiber inserted into the lumen of said tube serve as footholds for regeneration by nerve fibers, and nerve fibers use them for regenerating and extending.

As a preferable mode of the present invention, the tube 11 or 21 composed of a material that is biodegradable and absorbable in vivo is a tube composed of a mesh-like tube of polyglycolic acid, and a coating laye 23 (and also 22 depending on the case) of said tube is composed of amorphous collagen.

It is preferable that each of the fibers that composes the collagen fiber bundle be type I collagen fibers or mixed collagen fibers of Type I and Type III obtained by solubilizing collagen originating in the skin or bone and so forth of various animals used in the past with acid, base or enzyme, and that its diameter is preferably about 1–50 $\mu$m, particularly preferably about 5–10 $\mu$m. In the case of using the artificial tube for nerve of the present invention as an artificial tube for spinal cord, the diameter of collagen fibers 31 is preferably about 1–50 $\mu$m, and particularly preferably about 5–10 $\mu$m. The percentage of void (=(1−(cross-section area occupied by collagen fibers/cross-section area of tube lumen), to apply similarly hereinafter) of tube 10 or 20 is preferably about 70–99.999%, and particularly preferably about 90–99.99%. In the case of an artificial tube for spinal cord, the percentage of void is preferably about 70–99.999%, and particularly preferably about 90–99.99%. For example, in the case of a tube having an inner diameter of 4 mm, about 160 collagen fibers 31 having a diameter of about 10 $\mu$m are filled (percentage of void: 99.9%). In addition, it is preferable that the surface of these collagen fibers 31 be coated in advance with laminin, respectively (not shown).

The following provides a description of the method for producing the artificial tube for nerve of the present invention. In order to produce the artificial tube for nerve of the present invention in which the material that is biodegradable and absorbable in vivo is a mesh material composed of a material selected from the group consisting of polyglycolic acid, polylactic acid, copolymer of glycolic acid and lactic acid, copolymer of lactic acid and ε-caprolactone, polydioxanone and copolymer of glycolic acid and trimethylene carbonate, and having a coating layer 13 or 23 (and also 12 or 22 depending on the case) composed of gelatin or collagen on at least the outer surface of tube 11, tube 11 composed of a mesh material using polyglycolic acid and so forth for the raw material is first prepared. Although the tube 11 may be prepared by any method, a mesh tube having the above-mentiond thickness is obtained by, for example, weaving fibers of polyglycolic acid and so forth (having a diameter of, for example, 0.1 mm) into the shape of a cylinder. The prepared tube 11 is immersed in a solution of the above-mentioned collagen or gelatin and air-dried to form a collagen or gelatin coating layer 13 or 23 (and also 12 or 22 depending on the case) on at least the outer surface of tube 11 as well as on the inner surfaces of the mesh pores (In the case of forming said collagen or gelatin coating layer on only the outer surface of said tube and the inner surfaces of the mesh pores, prior to immersing in said solution or collagen or gelatin, a rod made of Teflon and so forth should be inserted into the lumen of said tube that makes contact with the inner surface of said tube). In order to coat tube 11 with collagen or gelatin, an approximately 1 N hydrochloric acid solution (pH of about 3) preferably containing about 1–3 wt %, and particularly preferably about 1–2 wt %, of collagen, or preferably an about 2–30 wt %, and particularly preferably about 10–20 wt %, aqueous gelatin solution is used. In addition, in the case of using tube 11 of a mesh material composed of polyglycolic acid and so forth for tube 11 or 12 composed of a material that is biodegradable and absorbable in vivo, it is convenient to coat the surface with collagen or gelatin after treating with plasma discharge, ozone irradiation and so forth to impart said material with hydrophilic properties.

In order to prepare the artificial tube for nerve of the present invention in which the material that is biodegradable and absorbable in vivo is a material composed of fine fibrous collagen, and a coating layer 23 (and also 22 depending on the case) of tube 21 is composed of collagen, a rod made of Teflon and so forth having, for example, a diameter of about 1–8 mm and preferably about 4 mm is used for the core. In the case of using the artificial tube for nerve of the present invention as an artificial tube for spinal cord, the rod having a diameter of preferably about 2–12 mm, and particularly preferably about 10 mm, is used. The core is immersed in an approximately 1 N hydrochloric acid solution containing preferably about 0.5–3 wt %, and particularly preferably about 1–2 wt %, of collagen, and a collagen hydrochloric acid solution layer having a thickness of preferably about 5–20 mm, and particularly preferably about 10 mm, is formed on the surface of said core followed by freezing (for example, at about 0° C. for about 12 hours). In the case of using the artificial tube for nerve of the present invention as an artificial tube for spinal cord, a collagen hydrochloric acid solution layer is formed having a thickness of preferably about 5–30 mm, and particularly preferably about 20 mm, followed by freezing. As a result of freezing, fine fragments of ice form between the collagen molecules dispersed in the hydrochloric acid solution, layer separation occurs in the collagen hydrochloric acid solution, and fine fibers are formed due to rearrangement of the collagen molecules. Next, this is further freeze-dried (for example, at about 0° C. for about 24 hours) in a vacuum. As a result of freeze-drying, in addition to the fine ice fragments between the collagen molecules vaporizing, a tube is obtained composed of a non-woven fabric-like collagen layer in which fine fibers overlap in multiple layers.

Next, the core on which is formed this fine fibrous collagen layer is placed in a pouch made of polyethylene and so forth, sealed and degassed followed by compression of the collagen layer. As a result of compressing, high-density, fine fibrous collagen layer 21 is obtained. Alternatively, the collagen layer may be compressed by pressing without degassing. Compression is performed such that the thickness of the collagen layer after compression is preferably about 0.5–5 mm, and particularly preferably about 1–2 mm. In the case of using as an artificial tube for spinal cord, compression is performed such that the thickness of the collagen layer is preferably about 0.5–5 mm, and particularly preferably about 1–3 mm. Furthermore, in the case of using that in which a collagen thread-like product is woven or knitted for the tube composed of fine fibrous collagen, in place of forming the above collagen hydrochloric acid solution layer, wet spinning is performed to first produce a collagen thread-like product after which this is woven or knitted into the shape of a tube. The remainder of the procedure starting with freeze-drying is the same as that described above.

Collagen membrane 23 (and also 22 depending on the case) is additionally formed on at least the outer surface of fine fibrous collagen layer 21 formed and compressed in the above manner. As a result of forming this collagen membrane 23 (and also 22 depending on the case), an artificial tube for nerve is obtained having even greater strength. In order to form this collagen membrane 23 (and also 22 depending on the case), the tube composed of fine fibrous collagen layer 21 removed from the above-mentioned rod is again immersed in an approximately 1 N hydrochloric acid solution containing preferably about 0.5–3 wt %, and particularly preferably about 1–2 wt %, collagen, and forming a collagen hydrochloric acid solution layer on at least the outer surface of fine fibrous collagen layer 21 followed by air-drying. This immersion and air-drying procedure is repeated several times, and preferably 5–20 times, to obtain collagen membrane 23 (and also 22 depending on the case) having an amorphous structure in which collagen molecules are dispersed (the thickness of the collagen hydrochloric acid solution layer is preferably about 0.2–1.0 mm, and particularly preferably about 0.5 m, overall). In the case of using the artificial tube for nerve of the present invention as an artificial tube for spinal cord, the thickness of collagen membrane 23 (and also 22 depending on the case) formed on at least the outer surface of fine fibrous collagen layer 21 is preferably about 0.2–1.0 mm, and particularly preferably about 0.5 m.

Tube 20 prepared in the manner can be handled easily and allows easy suturing with nerves due to its high tear strength as compared with a tube consisting of collagen membrane alone. A bundle of fibers composed of type I collagen or a mixture of type I and type III collagen is inserted substantially parallel to the axis of the tube into the lumen of tube 10 or 20 in which the coating layer 13 or 23 (and also 12 or 22 depending on the case) composed of collagen or gelatin are formed on at least the outer surface of tube 11 or 21 composed of a material that is biodegradable and absorbable in vivo prepared in the manner described above. As a result of inserting this collagen fiber bundle, nerve fibers are allowed to grow in cavities 32 between each of the collagen fibers that compose the fiber bundle, and in cavities 33 between collagen fibers 31 and the inner surface of tube 10 or 20 (and more accurately, on the surface of each collagen fiber 31 and on the inner surface of tube 10 or 20). Type I collagen or mixed Type I and Type III collagen fibers obtained by solubilizing collagen originating in the skin, bone and so forth of various animals used conventionally with acid, base or enzyme can be used for the collagen serving as the raw material of the collagen fiber bundles used here. The diameter of the collagen fibers used here is preferably about 1–50 $\mu$m, and particularly preferably about 5–10 $\mu$m, and collagen fibers are inserted so as to reach the above-mentioned percentage of void.

Next, crosslinking treatment is preferably performed on tube 10 or 20 composed of a material that is biodegradable and absorbable in vivo prepared in the manner described above (in the case of using tube 20, this crosslinking treatment is performed after preparing tube 21 and before forming the coating layer 13 or 23 (and also 12 or 22 depending on the case)). Crosslinking treatment is advantageous for the artificial tube for nerve of the present invention because it maintains the shape of the tube and prevents invasion of cells from outside the artificial tube for nerve during the time until the peripheral nerve is finished regenerating.

Although varying according to the length of the severed nerve portion that requires regeneration, crosslinking treatment is performed so an extent that the shape of the tube is retained for 1–3 months after application in the body. Although examples of crosslinking methods include gamma ray crosslinking, ultraviolet ray crosslinking, electron beam crosslinking, thermal dehydration crosslinking, glutaraldehyde crosslinking, epoxy crosslinking and water-soluble carbodiimide crosslinking, thermal dehydration crosslinking is preferable because it is easy to control the degree of crosslinking and does not have an effect on the body even when used for crosslinking treatment. Crosslinking treatment is performed in a vacuum at a temperature of, for example, about 105–150° C., preferably about 120–150° C., and particularly preferably about 140° C., for, for example, about 6–24 hours, preferably about 6–12 hours, and particularly preferably about 12 hours.

As mentioned above, it is preferable that prior to crosslinking treatment, each fiber of the collagen fiber bundle inserted into tube 10 or 20 composed of a material that is biodegradable and absorbable in vivo is coated in advance with a component that aids in the growth of nerve fibers. This component is preferably laminin, and particularly preferably human laminin. As an example of a method of accomplishing this, said collagen fiber bundle on which crosslinking treatment has been performed in advance is either immersed in a solution containing laminin dissolved in PBS, or a PBS solution of laminin is coated onto fibers composed of said collagen.

The artificial tube for nerve prepared in the manner described above can be used to restore nerve function by inserting both stumps of a nerve that has been severed by injury or surgical procedure into the present artificial tube for nerve and ligating those portions to induce axon regeneration and extension in the proper direction, and allow axons to reach from the peripheral nerve trunk to a neuromuscular junction or peripheral sensory receptor. In addition, in the case where the spinal cord is damaged due to injury as well, by removing the vertebrae corresponding to the damaged portion and covering the damaged portion of the spinal cord with the present artificial tube for nerve, it is believed that the damaged spinal cord can be regenerated and its function restored.

Although the following provides a detailed explanation of the present invention through its examples and comparative examples, the present invention is not limited to these.

EXAMPLE

Polyglycolic acid (PGA) fibers (diameter: 0.1 mm) were woven into a tubular shape to prepare a polyglycolic acid mesh tube (mesh pore size: approximately 100–200 $\mu$m) having a length of about 30 mm, inner diameter of about 4–5 mm and thickness of about 1 mm. By making its surface hydrophilic by subjecting to plasma discharge treatment and immersing this mesh tube in 1 N hydrochloric acid solution containing 1.0 wt % enzyme-solubilized collagen originating in pig skin and then air-drying, the outer and inner surfaces of the tube along with the inside surfaces of its mesh pores were coated with said collagen (immersion and drying procedure repeated 10 times).

Enzyme-solubilized collagen fibers originating in pig skin (diameter: approximately 5 μm) that were pretreated with thermal dehydration crosslinking (140° C.×24 hours) were immersed in a PBS solution of human laminin (concentration: 10 μg/ml) followed by air-drying (this procedure was repeated 3 times), and about 80 fibers of the resulting laminin-coated collagen were inserted into the tube obtained above having collagen coating layers on its inner and outer surfaces (percentage of void of the tube: 99.99%). Moreover, the tube was subjected to thermal dehydration crosslinking in a vacuum at 140° C. for 24 hours to obtain the artificial tube for nerve of the present invention.

25 mm of the sciatic nerve of a cat (body weight: 5 kg), 80 mm of the sciatic nerve of a dog (body weight: 10 kg) and 30 mm of the median nerve of a monkey (body weight: 15 kg) were respectively excised, the nerve stumps on both ends were inserted into the above-mentioned artificial tube for nerve and connected by ligating with 10-0 Nylon thread.

Recovery of nerve function was observed (by somatosensory evoked potential and evoked electromyograms) at 1 month after surgery in cat, 3 months after surgery in dog, and 2 months after surgery in monkey.

Comparative Example

With the exception of not inserting a collagen fiber bundle into the lumen of the tube, observations were in the same manner as the above example using the artificial tube for nerve prepared in the same manner as the example.

Recovery of function was not observed at the same number of days after surgery as in the example (although signs of recovery of function were observed at 3 months and 4 months in cat and monkey, respectively).

INDUSTRIAL APPLICABILITY

The artificial tube for nerve of the present invention is able to retain its shape until the nerve finishes regenerating. In addition, since it induces and promotes nerve regeneration, severed nerves regenerate faster and longer than in the case of conventional artificial tube for nerve, the state of the regenerated nerve more closely approaches the normal state, and recovery of nerve function is also favorable. In addition, it can also be used as an artificial tube for spinal cord for regeneration and recovery of damaged spinal cord.

What is claimed is:

1. An artificial tube for nerve comprising:
   a tube composing of a mesh material composed of a material selected from the group consisting of polyglycolic acid, polylactic acid, copolymer of glycolic acid and lactic acid, copolymer of lactic acid and ε-caprolactone, polydioxanone and copolymer of glycolic acid and trimethylene carbonate and having coating layers composed of gelatin or collagen on the inter and outer surfaces of said tube; and
   a collagen fiber bundle subjected to thermal dehydration corsslinking that is inserted into the lumen of said tube substantially parallel to the axis of said tube; wherein each of the fibers composing said collagen fiber bundle are coated with laminin.

2. The artificial tube for nerve according to claim 1, wherein said mesh material has a pore size of about 5–30 μm.

3. An artificial tube for nerve comprising:
   a tube of fine fibrous collagen and having coating layers composed or gelatin or collagen on the inner and outer surfaces of said tube; and
   a collagen fiber bundle subjected to thermal dehydration crosslinking that is inserted into the lumen of said tube substantially parallel to the axis of said tube; wherein each of the fibers composing said collagen fiber bundle are coated with laminin.

4. A method for producing the artificial tube for nerve according to any one of claims 1, 2 and 3 comprising the following steps
   preparing a collagen fiber bundle subjected to thermal dehydration crosslinking;
   coating the surface of each fiber composing said collagen fiber bundle with laminin;
   producing a tube composed of a mesh material composed of a material selected from the group consisting of polyglycolic acid, polylactice acid, copolymer of glycolic acid and lactic acid, copolymer of lactic acid and ε-caprolactone, polydioxanone, copolymer of glycolic acid and trimethylene carbonate, and fine fibrous collagen, and having coating layers composed of gelatin or collagen on the inter and outer surfaces of said tube;
   inserting said laminin-coated collagen fiber bundle so as to be substantially parallel to the axis of said tube; and followed by performing crosslinking treatment on said tube.

5. The method according to claim 4, wherein the filling density of said collagen fiber bundle is 90–99.99% when expressed as the percentage of void.

* * * * *